United States Patent [19]

Giger et al.

[11] Patent Number: 4,472,313

[45] Date of Patent: Sep. 18, 1984

[54] CYCLOPROPANATION OF OLEFINS

[75] Inventors: Urs Giger, Basel, Switzerland; Oljan Repic, Hopatcong, N.J.

[73] Assignee: Sandoz, Inc., E. Hanover, N.J.

[21] Appl. No.: 419,962

[22] Filed: Sep. 20, 1982

[51] Int. Cl.$^3$ ............................................. C09F 5/08
[52] U.S. Cl. .................................... 260/410; 560/124; 585/358
[58] Field of Search .................... 260/410 R; 560/124

[56] References Cited

U.S. PATENT DOCUMENTS

| | | | |
|---|---|---|---|
| 3,074,984 | 1/1963 | Simmons, Jr. ................... | 260/410 R |
| 3,211,561 | 10/1965 | Gearhart et al. ................ | 260/410 R |
| 3,766,218 | 10/1973 | Ueda et al. ...................... | 560/124 |
| 3,847,944 | 11/1974 | Ohno et al. ..................... | 560/124 |
| 3,957,849 | 5/1976 | Henrick et al. ................. | 260/410 R |
| 3,979,424 | 9/1976 | Searle et al. .................... | 560/124 |
| 3,997,586 | 12/1976 | Martel et al. ................... | 560/124 |

*Primary Examiner*—Y. Harris-Smith
*Attorney, Agent, or Firm*—Gerald D. Sharkin; Richard E. Vila; Frederick H. Weinfeldt

[57] ABSTRACT

The invention provides a method of converting ethylenically unsaturated units of an olefinic substrate to corresponding cyclopropanyl units, comprising treating the olefinic substrate, in an ether medium, with zinc and diiodomethane and a catalytic amount of a metallohydride reducing agent. Preferred substrates are olefinic fatty acids or their functional derivatives, e.g. oleic acid esters.

23 Claims, No Drawings

CYCLOPROPANATION OF OLEFINS

This invention relates to a chemical process, and in particular to an improved process for the conversion of an ethylenically unsaturated unit to a cyclopropanyl unit.

BACKGROUND

The conventional method of converting an olefinic position, i.e. an ethylenically unsaturated unit, to a cyclopropanyl unit, is known as the Simmons-Smith method and is described in J. Amer. Chem. Soc. 81, 4256 (1959). The conventional reaction involves the use of diiodomethane and a zinc-copper couple. The reaction medium is commonly an ether, such as diethyl ether. The conventional reaction as applied to a wide variety of olefinic compounds including ethylenically unsaturated fatty acid esters is described in Organic Reactions 20, 1 (1973).

THE INVENTION

The present invention comprises converting olefinic compounds to their corresponding cyclopropanyl-bearing derivatives by treatment of an olefinic compound in an ether medium with diiodomethane and metallic zinc, in the presence of a metallo-hydride reducing agent with agitation, under essentially anhydrous conditions.

The process of this invention can be represented as process (a), in the reaction scheme below:

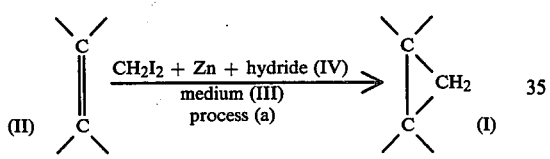

It will be noted that the zinc employed in process (a) is not in couple form as in the Simmons-Smith procedure. In process (a) the zinc is employed in a divided form, e.g. as a powder, such as zinc dust. Since zinc-copper couple is relatively difficult to prepare, its avoidance represents an advantageous savings in time and costs for this invention.

The olefinic compound II (substrate) may be a hydrocarbon having one (shown) or more ethylenically unsaturated positions e.g. an alkenyl compound, and may be optionally substituted by non-hydrocarbon functions. Where the substituent is inert under the reaction conditions of process (a), then the only difference between the substrate and the product of the reaction would be at the olefinic position:

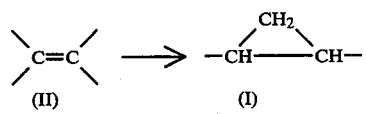

However, where the substituent is not inert, e.g. it could either be converted to some other desired function, or "protected" or "masked" by means which are well known in the art, during process (a), and then at a later time "deprotected" to obtain the desired product. For example, where a cyclopropanyl-bearing fatty acid is desired, the carboxylic acid function can be esterified, process (a) carried out and the resultant cyclopropanyl-bearing ester later saponified to obtain its corresponding free carboxylic acid. The substrate II may have one or more non-conjugated ethylenically unsaturated positions.

A wide variety of ethers (III) may be used as the reaction media for process (a) but the preferred ethers have boiling points of at least about 70° C. The ethers may be linear or cyclic, e.g. tetrahydrofuran or dioxane. Preferred ethers are linear ethers that have 2 or more e.g. up to 6, ether linkages. Especially preferred ethers are those of the formula IIIa:

in which q is 2 or 3, preferably 2, and each of $R^1$ and $R^2$ is, independently, lower alkyl having from 1 to 3 carbon atoms. While $R^1$ and $R^2$ can be unlike, they are preferably like, e.g. methyl. A particularly preferred ether is 1,2-dimethoxyethane, e.g. the dimethyl ether of ethylene glycol. A portion of the medium may be an aromatic hydrocarbon e.g. benzene and toluene or a non-aromatic hydrocarbon such as iso-octane. Preferably, the major portion of the medium is an ether.

While members of the general class of metallo-hydride reducing agents, may be employed, such as lithium aluminum hydride, or alkali metal borohydrides, the preferred metallic hydride reducing agents (IV) are those which are soluble in the ether medium, and more preferably organo-metallic hydrides of which preferred classes include those of formula IVa:

in which Y signifies an alkali or alkaline earth metal, e.g. sodium or lithium; and
each of $Z_1$, $Z_2$ and $Z_3$ is, independently, a hydrogen atom, or an alkyl or alkoxy radical of 1 to 6 carbon atoms; or an alkoxyalkoxy or alkyleneoxyalkyl radical having from 2 to 6 carbon atoms;

provided that at least one of $Z_1$, $Z_2$ and $Z_3$ is other than a hydrogen atom; or of formula IVb:

in which $Z_4$ and $Z_5$, which may be the same or different, each signify a hydrogen atom or an alkyl radical of 1 to 6 carbon atoms;

provided that at least one of $Z_4$ and $Z_5$ is alkyl.

The alkyl and alkoxy radicals mentioned above in connection with compounds of formula IVa and IVb are understood to include as the alkyl portion thereof methyl, ethyl, propyl, butyl, amyl and hexyl, including isomers where such exist, but are preferably unbranched; and the alkylene (and alkylene portions of alkyleneoxy) radicals are understood to include methylene, ethylene, n-propylene, n-butylene, n-amylene and n-hexylene radicals, including isomers where they exist, but are preferably unbranched.

With respect to compounds IVa Z, $Z_2$ and $Z_3$ may be the same or different but are preferably the same. With respect to the compounds IVb, $Z_4$ and $Z_5$, they may be the same or different, but are preferably the same.

Reaction temperatures may vary fairly widely. The reaction may be conducted at higher temperature of the order of 180° C., or lower temperatures in the order of 20° C., but such temperatures offer no significant advantages and therefore reaction temperature are usually in the range of from about 50° to 120° C., preferably from about 70° to 100° C., and more preferably from about 80° to 95° C.

A preferred hydride reagent IVa is sodium dihydridobis-(2-methoxyethoxy)aluminate, which is obtainable commercially under the brand name "Vitride", and has the structure IVa':

an important property of the hydride IVa' is that it is soluble in a variety of solvents.

Process (a) should be carried out under essentially anhydrous conditions and in the absence of proton-contributing agents, which could interfere with the reaction. The reaction is preferably carried out under an inert atmosphere, e.g. dry nitrogen.

In carrying out process (a) it is preferred that the zinc and diiodomethane reagents each be present in molar excess, e.g. in a molar ratio of from about 2 to 6 times preferably from about 3.5 to 5 that of the olefinic positions of the substrate (II). The hydride reducing agent (IV) however, need be present only in catalytic amounts, e.g. from about 0.5% to 3%, preferably from about 1.0 to 2.0%, of the molar amount of the olefinic positions of II.

Where the olefinic substrate (II) has a relatively low boiling point, the reaction may be carried out by employing refluxing conditions, or under pressure to achieve the reaction temperatures suitable to accomplish process (a). The process may be run batch-wise or adapted to a continuous system as is well understood in the art.

A preferred class of compounds I are those in which each of the ethylenically unsaturated positions of a naturally-occurring fatty acid e.g. oleic or linoleic acid (or derivative, e.g. an ester), is replaced by a cyclopropanyl group.

A particularly preferred class of Compounds I are those of the formula I':

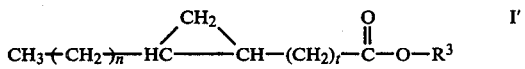

wherein $R^3$ is lower alkyl having from 1 to 4 carbon atoms, e.g. methyl or ethyl; n is a whole integer of from 0 to 19; and t is a whole integer of from 1 to 20, provided that n+t is from 4 to 20. It is preferred that each pair of hydrogen atoms bound to the tertiary carbon atoms of a cyclopropanyl group is in the cis configuration and in addition to the preferences discussed above, it is also preferred that the Compounds I' have one or more of the following characteristics: (1) n+t=7 to 20, (2) n+t= an even number, and (3) each of n and t is, independently, 3, 5 or 7, especially where each of n and t is 7.

Cyclopropanyl-bearing compounds of the general type of compounds I' are particularly useful intermediates in the preparation of amides and hydrazides which are useful in treating atherosclerotic conditions, as disclosed in U.S. Pat. Nos. 4,248,893 and 4,201,785.

Under the above-noted preferred conditions an advantage of the present invention is that very high conversion of the olefinic substrate is achieved, to give very high yields of the desired product. The desired product is therefore obtained in relatively pure form with minimal side-products, thus simplifying recovery procedures. For example, such refining techniques as distillation can therefore often be avoided. The advantageous savings in raw material costs, time and refining costs of this process will therefore be appreciated.

When carried out under the preferred conditions an additional advantage of the process of this invention is that "delayed exotherm" is avoided. Thus, the process can be readily adapted to large scale operations. When the conventional process is carried out on a small scale, the rapid rise in temperature as the reaction proceeds can be controlled by application of cooling techniques. However, as the scale of the operation increases toward commercially feasible proportions, such cooling techniques become more difficult to apply. The "delayed exotherm", thus constitutes a serious problem, and its avoidance can be seen to be a clear advantage of the process of this invention.

It is also advantageous in carrying out process (a) that ultrasonic irradiation be employed, to keep the zinc activated during the reaction. Analogous methods are reported in the literature e.g. Tetrahedron Letters 1982, 2729 and J. A. C. S. 1980, 7926, for activating zinc and magnesium, respectively, during organic reactions, e.g. as the zinc may be employed in less finely divided form, such as mossy zinc.

Compounds of the formulae II, III and IV are generally known, and those which may not be known may be prepared by adapting procedures reported in the literature for the preparation of their known analogs.

Compounds I may be recovered and refined, where such is desired, by conventional means, such as by crystallization, distillation or chromatographic techniques such as column or thin layer chromatography.

EXEMPLIFICATION

Examples are presented hereinafter as illustrative of the preparation of compounds of this invention. All temperatures are centigrade and room temperature is 20° to 30° C., unless indicated otherwise.

Example 1

Methyl cis-9,10-methyleneoctadecanoate*

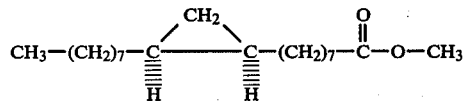

Into a 2 liter flask equipped with a stirrer, thermometer, nitrogen gas inlet, 125-ml addition funnel, external heating source and condenser (having a $CaCl_2$ drying tube) is added, under a nitrogen gas atmosphere, with stirring, 88.6 g (1.28 mol) of zinc dust and 400 ml of dry 1,2-dimethoxyethane. With stirring, 25 ml of a 70% (w/v) solution of sodium dihydrido-bis(2-ethoxymethoxy)aluminate (0.005 mol) in benzene is added dropwise. The mixture is heated to reflux (about 84°) and stirred for 15 minutes. 100 g (0.34 mol) of methyl oleate* is rapidly added (under $N_2$) to the reaction mixture, with stirring, followed by a rinse of the container which held the methyl oleate with 50 ml of dry 1,2-dimethoxyethane. The temperature first drops (to about 79°), but as stirring continues rises (to about 82°-83°), at which point 112 ml of diiodomethane (1.39 mol) is added cautiously dropwise (over a period of about 45 minutes) at such a rate that gentle reflux (with minimum foaming) is maintained. As the diiodomethane is added the temperature begins to rise (to about 84°) and the refluxing is controlled by lowering the external heating and regulating the rate of addition. By the end of the addition the temperature is about 94°. After addition is completed, reflux is maintained (by heating to temperature of about 94°) for 6½ hrs. The reaction mixture is then allowed to cool to about 20°–25°, and allowed to stand for about 18 hrs (optionally may be slowly stirred).

*also known as methyl ester of dihydrosterculic acid or methyl cis-2-octylcyclopropanoctanoate
**dried over 3A molecules sieves (to no more than 0.08% water), peroxide free.
***protect from air and light The vessel is then flushed with nitrogen gas, and 400 ml of toluene is added, with stirring. Ice cooling is applied to keep the temperature at about 20° to 30°, while 400 ml of 2N hydrochloric acid is cautiously added at such a rate that exothermic heating and foaming (due to release of hydrogen) are controlled. At this point the excess zinc is almost entirely dissolved.

The liquid is separated into layers in a separatory funnel and the organic layer set aside for later combining. The aqueous phase (reddish-brown color) is extracted twice with 400-ml portions of toluene. The organic portions are then combined (for a total of about 1,600 ml), and washed with water (twice with 400 ml, then with 200-ml portions as needed) until the water wash is about pH 6. The organic phase is then dried by stirring with about 150 g of anhydrous sodium sulfate, then filtered (via Buchner funnel, which is then rinsed with 400 ml of toluene in portions), and the combined organic phase (pale yellow) concentrated by evaporation under vacuum (rotary evaporator; at about 40°–50°, 20 mm Hg) to obtain a pale yellow oil which consists of the title compound and a small amount of toluene, which is satisfactory for many uses as an intermediate, but can be further refined if desired by subjecting to high vacuum drying to remove the toluene. The product of this example on gas chromatographic analysis shows 95% methyl cis-9,10-methyleneoctadecanoate, about 2.5% of the trans isomer, about 1% starting material, and about 1.5% by-products.

Example 2

Repeating the procedure of Example 1, but using in place of the methyl oleate, an approximately equivalent amount of:
(a) ethyl oleate;
(b) ethyl linolate (ratio of reagents doubled); or
(c) ethyl trans-9-octadecenoate;
there is accordingly obtained:
(a) ethyl cis-9,10-methyleneoctadecanoate (as in oil);
(b) ethyl cis,cis-9,10,12,13-dimethyleneoctadecanoate; and
(c) ethyl trans-9,10-methyleneoctadecanoate.

Example 3

Methyl cis,cis-9,10,12,13-dimethyleneoctadecanoate $$CH_3-(CH_2)_4-\overset{\triangle}{\underset{H\ \ H}{=\!=}}-CH_2-\overset{\triangle}{\underset{H\ \ H}{=\!=}}-(CH_2)_7-\overset{O}{\underset{\|}{C}}-OCH_3$$

Repeating the procedure of Example 1, but using in place of the methyl oleate, an approximately equivalent amount of methyl linolate (and ratio of reagents doubled) there is accordingly obtained methyl cis,cis-9,10,12,13-dimethyleneoctadecanoate (as an oil).

What is claimed is:

1. A method of preparing a compound bearing one or more non-conjugated cyclopropanyl radicals of the structure I:

$$\diagdown_C\diagup^{CH_2}\diagdown_C\diagup \quad \text{I}$$

which comprises reacting in an ether medium, under essentially anhydrous conditions, with agitation, a substrate compound bearing one or more corresponding ethylenically unsaturated radicals of the formula II:

$$\diagdown_C=C\diagup \quad \text{II}$$

with divided zinc and diiodomethane in the presence of a catalytic amount of a metallo-hydride reducing agent, provided that the remaining substituents of the substrate are inert under said reaction conditions.

2. The method of claim 1 in which the metallo-hydride reducing agent is soluble in the ether medium.

3. The method of claim 2 in which the metallo-hydride reducing agent is of the formula:

$$Y^\oplus \quad Z_1-\underset{\underset{Z_3}{|}}{\overset{\overset{Z_2}{|}}{Al}}-H$$

in which Y signifies an alkali or alkaline earth metal; and
each of $Z_1$, $Z_2$ and $Z_3$ is, independently, a hydrogen atom, or an alkyl or alkoxy radical of 1 to 6 carbon atoms; or an alkoxyalkoxy or alkyleneoxyalkyl radical having from 2 to 6 carbon atoms;
provided that at least one of $Z_1$, $Z_2$ and $Z_3$ is other than a hydrogen atom; or of the formula:

$$Z_5-\underset{}{\overset{\overset{Z_4}{|}}{Al}}-H$$

in which $Z_4$ and $Z_5$, each is, independently, a hydrogen atom or an alkyl radical of 1 to 6 carbon atoms; provided that at least one of $Z_4$ and $Z_5$ is alkyl.

4. The method of claim 6 in which the metallo-hydride reducing agent is sodium dihydrido-bis(2-ethoxymethoxy) aluminate.

5. The method of claim 1 in which the ether medium has a boiling point of at least 70° C.

6. The method of claim 5 in which the ether (ii) has the formula:

$$R^1-O-(CH_2)_q-O-R^2$$

in which q is 2 or 3, and each of $R^1$ and $R^2$ is, independently, lower alkyl having from 1 to 3 carbon atoms.

7. The method of claim 6 in which $R^1$ and $R^2$ are the same.

8. The method of claim 6 in which q is 2.

9. The method of claim 8 in which the ether is 1,2-dimethoxyethane.

10. The method of claim 1 in which the temperature of the reaction is from about 20° to 180° C.

11. The method of claim 10 in which the temperature is from about 70° to 100° C.

12. The method of claim 10 in which the temperature is from about 80° to 95° C.

13. The method of claim 1 in which the compound has the formula:

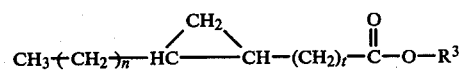

wherein n is a whole integer of from 0 to 19; and t is a whole integer of from 1 to 20, provided that n+t is from 4 to 20 and $R^3$ is lower alkyl.

14. The method of claim 13 in which each of the hydrogen atoms of the pair of tertiary carbon atoms of the cyclopropanyl unit are in the cis configuration.

15. The method of claim 13 in which n and t of the compound are each 7.

16. The method of claim 13 in which n+t is from 7 to 20.

17. The method of claim 13 in which the compound is methyl cis-9,10-methyleneoctadecanoate.

18. A method of claim 1 in which the compound is methyl cis,cis-9,10,12,13 dimethyleneoctadecanoate.

19. The method of claim 1 in which the zinc is in the form of zinc dust.

20. A method of claim 1 in which the substrate compound is a naturally-occurring fatty acid or derivative thereof.

21. A method of claim 20 in which the substrate compound is an ester of a naturally-occurring fatty acid.

22. A method of claim 20 in which the fatty acid is oleic acid.

23. A method of claim 20 in which the fatty acid is linoleic acid.